United States Patent [19]

Eibl et al.

[11] 4,163,748
[45] Aug. 7, 1979

[54] PROPANE-1,3-DIOL PHOSPHATIDES AND METHOD OF PREPARING THE SAME

[75] Inventors: Hansjörg Eibl, Bovenden; Alfar Nicksch, Goettingen-Nikolausberg, both of Fed. Rep. of Germany

[73] Assignee: Max-Planck-Gesellschaft zur Forderung der Wissenschaften E.V., Goettingen, Fed. Rep. of Germany

[21] Appl. No.: 846,717

[22] Filed: Oct. 31, 1977

Related U.S. Application Data

[63] Continuation of Ser. No. 689,538, May 24, 1976, abandoned, which is a continuation of Ser. No. 501,135, Aug. 28, 1974, abandoned.

[30] Foreign Application Priority Data

Sep. 6, 1973 [DE] Fed. Rep. of Germany ....... 2345057

[51] Int. Cl.$^2$ .................... A23J 7/00; C07F 9/02
[52] U.S. Cl. ....................... 260/403; 252/356
[58] Field of Search .......................................... 260/403

[56] References Cited

U.S. PATENT DOCUMENTS

| | | | |
|---|---|---|---|
| 3,542,876 | 11/1970 | Blaney | 260/583 |
| 3,694,473 | 8/1972 | Eibl | 260/403 |
| 3,694,474 | 8/1972 | Eibl | 260/403 |
| 3,882,181 | 5/1975 | Forster et al. | 260/583 N |

*Primary Examiner*—John Niebling
*Attorney, Agent, or Firm*—Toren, McGeady and Stanger

[57] ABSTRACT

Propane-1,3-diol phosphatides of the formula

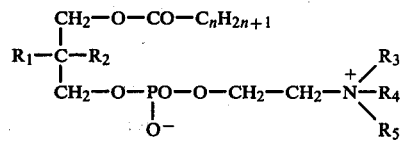

are prepared from the corresponding 1-alkanoyl-propanediols by conversion to an intermediate alkanoyl-propanediol-phosphoric acid β-bromoethyl ester with β-bromoethylphosphoric acid dichloride, and amination of the intermediate. They are biodegradable surfactants useful in detergent compositions and as emulsifiers in foods. In the formula, n is an integer and 9 to 25, $R_1$ and $R_2$ may be hydrogen or alkyl having up to six carbon atoms, and $R_3$, $R_4$, $R_5$ may be hydrogen or methyl, but at least one of $R_3$, $R_4$, and $R_5$ is hydrogen when $R_1$ and $R_2$ are both hydrogen.

6 Claims, No Drawings

PROPANE-1,3-DIOL PHOSPHATIDES AND METHOD OF PREPARING THE SAME

This is a continuation of application Ser. No. 689,538, filed May 24, 1976, and now abandoned, itself a continuation of abandoned application Ser. No. 501,135, filed Aug. 28, 1974.

This invention relates to propanediol phosphatides, and particularly to propane-1,3-diol phosphatides and to a method of preparing the same.

More specifically, the invention relates to a method of preparing propane-1,3-diol phosphatides of the formula

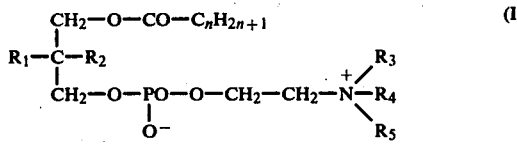

wherein n is an integer, and 9 to 25, and particularly between 12 and 18, $R_1$ and $R_2$ may be hydrogen or alkyl having up to six carbon atoms, and $R_3$, $R_4$, and $R_5$ may be hydrogen or methyl, at least one of $R_3$, $R_4$, and $R_5$ being hydrogen when $R_1$ and $R_2$ both are hydrogen.

The compounds of Formula (I) are prepared by reacting the corresponding 1-alkanoyl derivatives of propane-1,3-diol having the formula

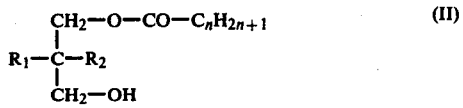

with β-bromoethylphosphoric acid dichloride (O=PCl$_2$—O—CH$_2$—CH$_2$—Br) to an intermediate of the formula

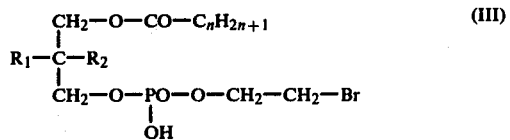

which intermediate, when reacted with an aminating agent of the formula

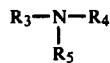

yields the compound of Formula (I), the meaning of n and $R_1$-$R_5$ being the same in all formulas.

The alkanoyl derivatives of propane-1,3-diol and of its 2-alkyl substitution products (Formula II) are readily prepared from the diols by reaction with alkanoyl chlorides or alkanoic acid anhydrides in a conventional manner. The acylation reaction is advantageously carried out in an anhydrous polar organic solvent or solvent mixture. A mixture of chloroform and pyridine in a ratio of 3:1 to 1:3 is the preferred medium. The reaction readily occurs at normal room temperature (15°–25° C.), but may be hastened by somewhat raising the reaction temperature.

The reaction between the alkanoyl derivatives of Formula (II) and β-bromoethylphosphoric acid dichloride is also carried out under anhydrous conditions, an organic solvent medium being employed, and chloroform being preferred. The reaction proceeds best in the presence of an amine, more than one mole of the amine being preferably present per mole of the phosphoric acid derivative. Triethylamine has been found to favor particularly high yields of the intermediate of Formula (III).

The intermediate is reacted with ammonia or an amine in a mixture of solvents at any temperature at which the mixture is liquid, temperatures below 0° C. usually resulting in reaction rates which are too low to be economically attractive. The preferred solvent mixtures consist of chloroform and acetonitrile or nitromethane. The solvent mixture may additionally contain a lower alkanol having up to four carbon atoms and water for better solubility of the reactants.

The desired phosphatides are produced in good yields in a sequence of relatively simple operations from starting materials which are commercially available at reasonable cost.

The invention also relates to compounds of the formula

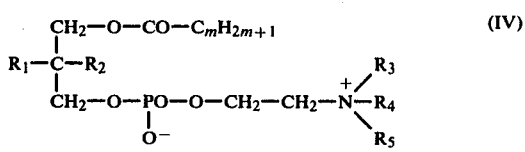

wherein m is an integer and 9 to 25, and $R_1$ to $R_5$ are as defined above, at least one of $R_3$, $R_4$, and $R_5$ being hydrogen when $R_1$ and $R_2$ are both hydrogen.

The compounds of the invention are white, microcrystalline powders lacking a well-defined melting point. They can be identified by thin-layer chromatography and elemental analysis.

They are biodegradable surfactants suitable for use in detergents and as emulsifiers in foods such as margarine. They also have the ability of modifying the properties of cell membranes in a manner to improve the effects of therapeutic agents.

Enzymes in cell membranes contain mixtures of natural phospholipids which include unsaturated aliphatic acid moieties. Because of the instability of these unsaturated moieties in the presence of oxygen, the enzymes are not stable when isolated. When the enzymes are stripped of their natural lipid component, they lose their enzyme activity, but the delipidized enzymes can be reactivated in stabilized condition by mixing them with the compounds of the invention.

It is thought by biologists that hybrid formation and cell fusion are induced by lysolocithin so that cell hybrids may be produced as by Sendai virus. However, the lysolocithins employed in this work are derived from egg lecithin and have substantial cytolytic activity. Cytolysis can be avoided by using compounds of the invention selected for suitable cytolytic activity.

The following Examples are further illustrative of this invention.

EXAMPLE 1

A solution of 100 g (0.36 mole) palmitoyl chloride in 400 ml anhydrous chloroform was added dropwise with stirring to a solution of 100 g (0.96 mole) 2,2-dimethylpropane-1,3-diol in a mixture of 200 ml anhydrous chloroform and 100 ml pyridine. Stirring of the resulting mixture was continued for one hour, and the solvent was removed in a rotary evaporator. A pyridinebearing oil was obtained and was stirred into a mixture of 1.5 liter 0.3 N sulfuric acid and one kilogram ice.

A white precipitate of palmitoyl-2,2-dimethyl-propane-1,3-diol formed, was filtered off with suction, dried, and recrystallized from hexane. The pure product weighed 80 g (65% yield based on the palmitoyl chloride), had a melting point of 39° C., and was identified by elemental analysis.

Calculated: 73.63% C; 12.36% H; Found: 73.78; 12.39.

49 g β-Bromoethylphosphoric acid dichloride (0.2 mole) and 40 g anhydrous triethylamine (0.4 mole) were dissolved in 150 ml anhydrous chloroform at about 0° C. The phosphorylation mixture was permitted to assume room temperature (about 18° C.), and a solution of 50 g palmitoyl-2,2-dimethyl-propane-1,3-diol (0.14 mole) in 250 ml anhydrous chloroform was added dropwise with stirring. Stirring then was continued until palmitoyl-2,2-dimethyl-propane-1,3-diol could no longer be detected by thin layer chromatography (2–3 hours). The phosphorylation mixture then was mixed with an equal volume of ice and stirred 20 minutes to hydrolyze the phosphoric acid chlorides present.

The chloroform layer was separated from the aqueous liquid present, dried over desiccated sodium sulfate, and evaporated to dryness. A crude palmitoyl-2,2-dimethyl-propane-1,3-diol-phosphoric acid β-bromoethyl ester was obtained in an amount of 52 g. A sample of the crude intermediate was purified by column chromatography and identified by elemental analysis.

Calculated: 50.45% C; 8.83% H; 14.6% Br; 5.66% P; Found: 50.73; 9.16; 13.8; 5.66.

The crude intermediate was dissolved in 50 ml chloroform in an amount of 5 g (10 millimoles), and 100 ml acetonitrile, 100 ml methanol, and 100 ml 25% aqueous ammonia were sequentially added to the solution. The reaction mixture was held in a sealed flask for 24 hours at 49° C., and stripped of volatile solvent in a rotary evaporator. The residue was taken up in 100 ml chloroform, 120 ml methanol, and 100 ml 2% formic acid solution with vigorous shaking. The chloroform phase then was separated from the aqueous liquid, washed with 100 ml 0.1-molar aqueous sodium acetate solution (pH 5.6) and 120 ml methanol to neutralize the formic acid, and thereafter stirred with 10 g sodium sulfate. The desiccant was filtered off, the solvent was evaporated, and the residue was recrystallized from methylethylketone. It was further purified by chromatography on silica gel.

White, pure O-(1-palmiteyl-2,2-dimethyl-propane-1,3-diol-phosphoryl)-ethanolamine was recovered in an amount of 3.6 g (57% yield based on palmitoyl-2,2-dimethyl-propane-1,3-diol) and identified by elemental analysis.

Calculated: 59.33% C; 10.39% H; 3.01% N; 6.65% P; Found: 58.97; 10.47; 3.07; 6.49.

EXAMPLE 2

When methylamine was substituted in an equimolecular amount for the ammonia in the procedure of Example 1, 5 g (10 millimole) of the intermediate β-bromoethyl ester was converted to 3.5 g pure O-(1-palmitoyl-2,2-dimethyl-propane-1,3-diol-phosphoryl)-N-methylethanolamine (52% yield) which was identified by elemental analysis.

Calculated: 60.10% C; 10.51% H; 2.92% N; 6.46% P; Found: 59.85; 10.58; 2.95; 6.35.

EXAMPLE 3

5 g (10 Millimole) intermediate β-bromoethyl ester, prepared as in Example 1, was reacted with an amount of trimethylamine equivalent to the methylamine employed in Example 2 as described in the preceding Examples, and the reaction product was purified by chromatography as in Example 1. 4 g O-(1-Palmitoyl-2,2-dimethyl-propane-1,3-diol-phosphoryl)-choline (57% yield) was recovered and identified by elemental analysis.

Calculated: 59.40% C; 10.74% H; 2.66% N; 5.89% P; Found: 58.73; 10.92; 2.94; 6.22.

EXAMPLE 4

The compounds of Formula (I) listed in the following Table were prepared in the manner of Examples 1 to 3 from the β-bromoethyl esters of the respective 1-alkanoyl-propane-1,3-diol-phosphoric acids and 1-alkanoyl-2,2-alkyl-propane-1,3-diol-phosphoric acids. The 1-lauroyl, 1-palmitoyl, and 1-arachoyl derivatives were prepared in each instance and identified by elementary analysis, "Alkanoyl" in the Table thus represents lauroyl, palmitoyl, and arachoyl.

TABLE

O-(1-Alkanoyl-propane-1,3-diol-phosphoryl)-N-methylethanolamine

O-(1-Alkanoyl-propane-1,3-diol-phosphoryl)-N,N-dimethylethanolamine

O-(1-Alkanoyl-2,2-dimethyl-propane-1,3-diol-phosphoryl)-ethanolamine

O-(1-Alkanoyl-2,2-dimethyl-propane-1,3-diol-phosphoryl)-N-methylethanolamine

O-(1-Alkanoyl-2,2-dimethyl-propane-1,3-diol-phosphoryl)-N,N-dimethylethanolamine O-(1-Alkanoyl-2,2-dimethyl-propane-1,3-diol-phosphoryl)-choline O-(1-Alkanoyl-2-ethyl-2-methyl-propane-1,3-diol-phosphoryl)-ethanolamine O-(1-Alkanoyl-2-ethyl-2-methyl-propane-1,3-diol-phosphoryl)-N-methylethanolamine O-(1-Alkanoyl-2-ethyl-2-methyl-propane-1,3-diol-phosphoryl)-N,N-dimethylethanolamine O-(1-Alkanoyl-2-ethyl-2-methyl-propane-1,3-diol-phosphoryl)-choline O-(1-Alkanoyl-2,2-diethyl-propane-1,3-diol-phosphoryl)-ethanolamine O-(1-Alkanoyl-2,2-diethyl-propane-1,3-diol-phosphoryl)-N-methylethanolamine

What is claimed is:

1. A method of preparing a phosphatide of the formula $$\begin{array}{c} CH_2-O-CO-C_nH_{2n+1} \\ | \\ R_1-C-R_2 \\ | \\ CH_2-O-PO-O-CH_2CH_2-N^+ \diagdown R_4 \\ | \\ O^- \end{array} \begin{array}{c} R_3 \\ \diagup \\ R_5 \end{array}$$

which comprises:

(a) reacting an alkanoyl derivative of propane-1,3-diol of the formula

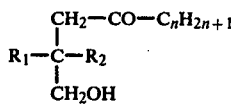

with β-bromoethylphosphoric acid dichloride of the formula $$O=PCl_2-O-CH_2CH_2-Br$$

until an intermediate of the formula

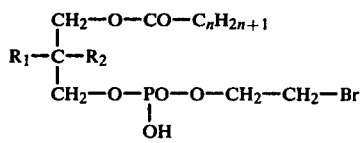

is formed; and (b) reacting said intermediate in a liquid medium essentially consisting of chloroform and a member of the group consisting of acetonitrile and nitromethane with an aminating agent of the formula

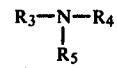

until said phosphatide is formed;

in said formulas, n being an integer between 9 and 25, $R_1$ and $R_2$ being hydrogen or alkyl having one to six carbon atoms, $R_3$, $R_4$, $R_5$ having hydrogen or methyl, at least one of said $R_3$, $R_4$, $R_5$ being hydrogen.

2. A method as set forth in claim 1, wherein said alkanoyl derivative is reacted with said β-bromoethylphosphoric acid dichloride in a liquid, anhydrous, organic medium.

3. A method as set forth in claim 1, wherein said liquid medium additionally includes water and an alkanol having up to four carbon atoms.

4. A method as set forth in claim 1, wherein $R_1$ and $R_2$ are alkyl and $R_5$ is hydrogen.

5. A method as set forth in claim 1, wherein $R_4$ and $R_5$ are hydrogen.

6. A method as set forth in claim 5, wherein $R_3$ is hydrogen.

* * * * *